United States Patent [19]

Weber, Jr.

[11] Patent Number: 5,332,841
[45] Date of Patent: Jul. 26, 1994

[54] PREPARATION OF 2,3-DIHYDRO-2,2-DIMETHYL-7-BENZOFURANYL CHLOROFORMATE WITH AQUEOUS PHASE REMOVAL

[75] Inventor: Harry W. Weber, Jr., Newtown, Pa.

[73] Assignee: FMC Corporation, Philadelphia, Pa.

[21] Appl. No.: 85,239

[22] Filed: Jun. 30, 1993

[51] Int. Cl.$^5$ .................................. C07D 307/86
[52] U.S. Cl. .................................................. 549/470
[58] Field of Search ........................................ 549/470

[56] References Cited

U.S. PATENT DOCUMENTS 5,066,819 11/1991 Kulkarni et al. ................... 549/470

OTHER PUBLICATIONS

Chemical Abstract 57:11106d (1962); Ger. 1,117,598, Nov. 23, 1961.

Chemical Abstracts 59:4139f (1963); Belg. 625,406, Mar. 14, 1963.

Chemical Abstracts 59:11673c (1963); Yuki Gosei Kagaku Kyokai Shi 21(8) 611–16 (1963).

Reasenberg and Goldberg, "Esters of β-Alkyaminoethanols", Journal of the American Chemical Society, 67, 933–9 (1945).

*Primary Examiner*—Bernard Dentz
*Attorney, Agent, or Firm*—N. L. Craig; R. M. Kennedy; R. L. Andersen

[57] ABSTRACT

A process for the production of 2,3-dihydro-2,2-dimethyl-7-benzofuranyl chloroformate which comprises treating 2,3-dihydro-2,2-dimethyl-7-benzofuranol and phosgene in a water immiscible organic medium with aqueous base and removing aqueous phase from the organic phase during the process.

13 Claims, 1 Drawing Sheet

PREPARATION OF 2,3-DIHYDRO-2,2-DIMETHYL-7-BENZOFURANYL CHLOROFORMATE WITH AQUEOUS PHASE REMOVAL

This invention relates to the production of insecticides. More particularly it pertains to an improved process for the production of 2,3-dihydro-2,2-dimethyl-7-benzofuranyl chloroformate which may be utilized in the production of the insecticide 2,3-dihydro-2,2-dimethyl-7-benzofuranyl N-methylcarbamate.

In accordance with the present invention there is provided an improved process for the production of 2,3-dihydro-2,2-dimethyl-7-benzofuranyl chloroformate (chloroformate) which comprises treating 2,3-dihydro-2,2-dimethyl-7-benzofuranol (benzofuranol) and phosgene in a water immiscible organic medium with aqueous base and removing aqueous phase from the organic phase during the process. Removal of the aqueous phase reduces the consumption of both phosgene and aqueous base thereby reducing raw material consumption and waste brine formation. Additionally this invention decreases the formation of bis(2,3-dihydro-2,2-dimethyl-7-benzofuranyl) carbonate (carbonate).

The chloroformate produced in this process can be treated without isolation, with aqueous methylamine and base to give high yields of the insecticide 2,3-dihydro-2,2-dimethyl-7-benzofuranyl N-methylcarbamate (carbamate).

The reaction zone in which the benzofuranol is converted to chloroformate may be contained in any suitable reactor which preferably does not impede thorough agitation. The process is preferably conducted in a glass or glass lined reactor which is fitted with an aqueous phase removal system, a condenser, inlet and sampling ports, and an agitating means. Reactor size does not appear to be critical to the successful use of the process. Reactors of 1 liter, 18.8 liters, and 114 liters have been used effectively. A standard 114 liter Pfaudler ®or similar type reactor equipped with a finger baffle is preferred. In commercial operations, scale-up of the Pfaudler type reactor to 4000 to 15,000 liters would be preferred.

Sufficient means for agitation should be provided to mix the aqueous phase with the organic phase. Excess agitation appears to adversely effect the reaction. The suitability of any particular agitation will depend on the size and configuration of the reactor and is best determined by routine optimization of the product yield and reactant consumption. In the above noted 114 liter Pfaudler reactor, a retreating blade agitator of 200 square centimeters rotating at 75 to 125 revolutions per minute is preferred. An agitation speed at the low end of this range appears to give the best results.

Removal of the aqueous phase may be accomplished by circulating the organic and aqueous phases through an aqueous phase removal system such as a liquid-liquid separator, and returning the organic phase to the reaction zone. Circulation has been effectively performed using a Teflon ® diaphragm pump connected with Teflon lined hose. Suitable liquid-liquid separators include both centrifugal separators and gravity settlers such as decanters. An internal or external decanter may be suitable. Commercially acceptable systems are within the skill of the art. The shape, size, and type of separator which is most suitable will depend on the other equipment in the system and the particular process parameters. The above noted 114 liter Pfaudler reactor system effectively utilized a 40 liter vertical cylindrical glass decanter equipped with a central input and terminal outflows. Preferably the decanter is charged with water before circulating the reactor contents. A water feed may be introduced into the aqueous phase in the decanter to adequately dissolve the salts carried over from the reactor. The water feed is preferred if the concentration of aqueous base used in the process is 25% or greater.

Typically 5% to 40%, and preferably 15% to 30% of the organic phase will pass through the separator per minute. With the organic phase will be carried aqueous phase, preferably mixed in the organic phase. Within the separator, aqueous phase is retained and then may be drawn off and sent to waste. The organic phase is circulated back to the reactor. The weight/weight ratio of water/medium in the reactor is best maintained below 0.1, preferably below 0.05, and more preferably below 0.02.

Aqueous phase is preferably removed during aqueous base addition. However aqueous phase removal during aqueous base addition need not be continuous or operate during the entire addition time. The aqueous phase removal system may be started before aqueous base is introduced into the reactor, or in another preferred mode, aqueous phase removal may begin immediately thereafter. Removal may be continued until the feed of aqueous base has been stopped, or preferably until aqueous phase is no longer being effectively removed. Most preferably aqueous phase removal should be maintained to such an extent as to avoid unacceptable phosgene hydrolysis.

The reaction may be carried out at temperatures from about $-10°$ C. to $40°$ C. A temperature range of $10°$ C. to $25°$ C. is preferred. A reaction temperature maintained within three degrees of $20°$ C. is most preferred. Reactions are preferably carried out at atmospheric pressure, but pressure is not a critical parameter.

The medium in which this process is conducted is one in which the benzofuranol and the chloroformate are at least partially soluble under the reaction conditions. The medium must be substantially immiscible with water. Suitable media include aromatic hydrocarbons such as benzene, toluene, isopropylbenzene and the xylenes; halobenzenes such as chlorobenzene; alkanes such as pentane, the hexanes, heptanes, and octanes; haloalkenes such as perchloroethylene; and haloalkanes such as trichloroethane and chloroform. Toluene and o-xylene are the media of preference.

The weight/weight ratio of benzofuranol to medium may be 0.1 to 0.35. Preferably the ratio is such that the benzofuranol is completely dissolved in the medium. A ratio of 0.2 to 0.3 is preferred.

Phosgene is preferably added to the benzofuranol-medium mixture as a liquid. Generally all the phosgene required by the reaction is added at one time. If the phosgene is depleted before complete conversion of the benzofuranol, additional phosgene may be added to complete the conversion. Alternatively, less than the required amount of phosgene may be added initially, and additional amounts may be added as the reaction progresses. Preferably additions should be frequent enough to ensure that phosgene is not depleted until the conclusion of the reaction, for example until more than 95% and preferably more than 99% of the benzofuranol has been consumed. Phosgene may also be added to the reaction mixture as a more or less continuous flow, with or without a separate initial charge of phosgene. Preferably phosgene should be added at such a rate that it is not depleted until the conclusion of the reaction. The amount of phosgene added to the system should be adequate to convert the benzofuranol to the chloroformate. A 1.1 to 2.0 mole ratio of phosgene to benzofuranol may be required. A mole ratio of 1.2 to 1.7, and particularly a 1.3 ratio may be used for an initial charge. The amounts charged incrementally or added through a flow system may best be determined by monitoring reactant concentrations as the reaction progresses.

The aqueous base with which the phosgene-benzofuranol-medium mixture is treated is preferably a 20-50% (wt/wt) aqueous sodium hydroxide solution. Concentrations of 25%, 30% and 40% have been used effectively. The aqueous base is best added at a rate which maintains the temperature of the reaction within the desired limits. Preferably the aqueous base is pumped into the reactor without appreciable change in the feed rate. A suitable rate of addition will depend on reactor size, the heat exchange system and other experimental parameters, and may be determined by routine optimization. Addition times below 3 hours are preferred, and below 2 hours are more preferred. The rate of aqueous base addition may be changed during the process, and addition may even be discontinued for periods of time. Addition of aqueous base should be continued until the pH of the reaction mixture permanently rises above pH 7, or until the phosgene or benzofuranol has been consumed. Preferably the equivalent ratio of base consumed to benzofuranol starting material will be 1.5 or less.

Upon completion of the reaction, the 2,3-dihydro-2,2-dimethyl-7-benzofuranyl chloroformate may be separated and purified using standard techniques known in the art. For example, in a preferred mode water is charged to the reactor, and is stirred with the organic phase. The amount of water used is not critical although enough should be present to dissolve solidified salts and destroy residual phosgene. Stirring is preferably continued until the phosgene concentration falls below 500 parts per million. The organic and aqueous layers are separated, and the aqueous layer is drawn off or removed by circulating the reactor contents through the liquid-liquid separator. The chloroformate may then be isolated from the medium using standard techniques which are known in the art.

In a preferred mode, the chloroformate is not isolated from the medium. Instead it is treated with aqueous methylamine followed by treatment with aqueous sodium hydroxide to give the insecticide 2,3-dihydro-2,2-dimethyl-7-benzofuranyl N-methylcarbamate.

The process of this invention is further illustrated in Examples 2 and 4. Examples 1 and 3 which do not include the inventive concept are included for comparison purposes.

EXAMPLE 1

Figure 1:
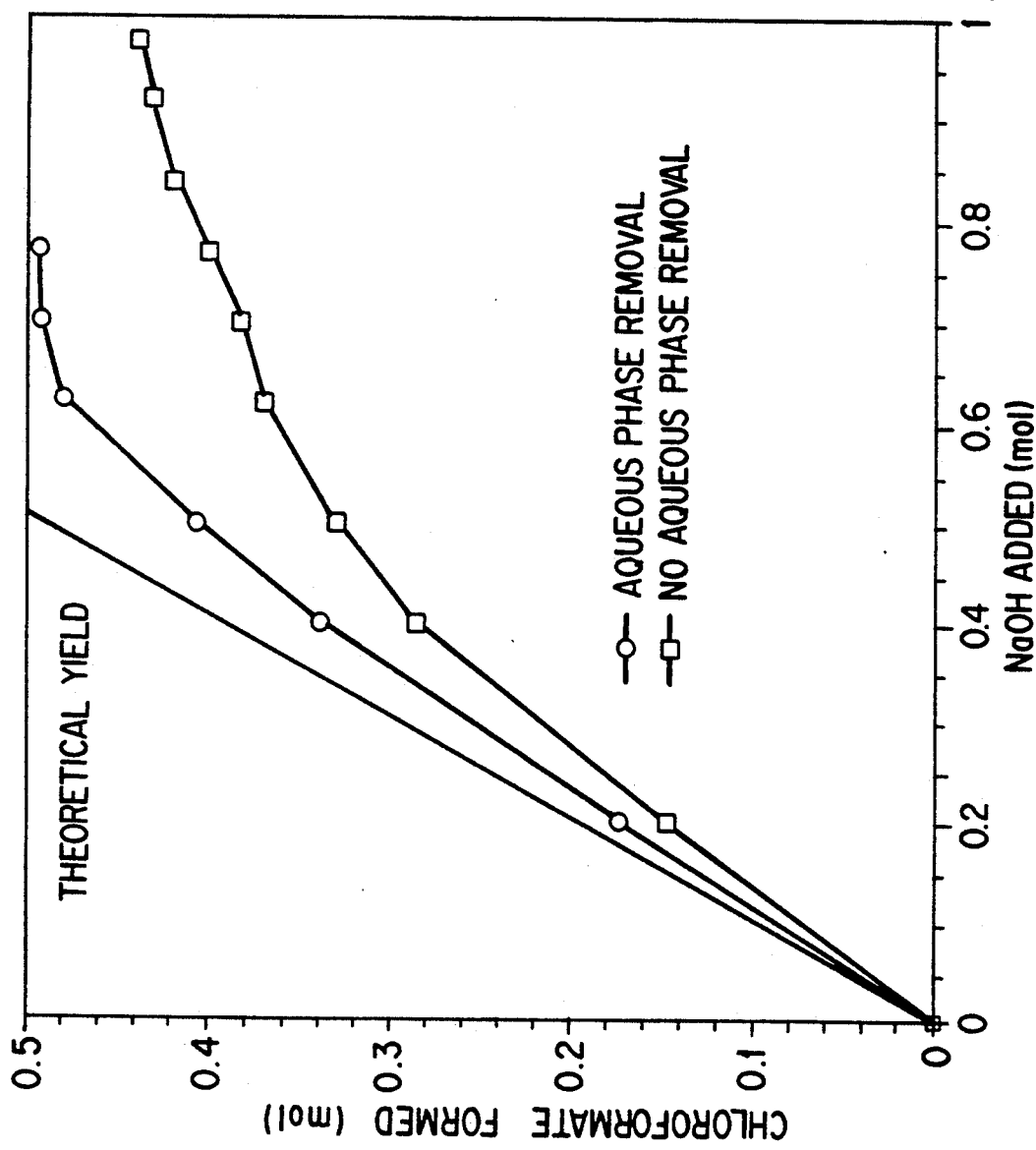
FIG. 1 compares the yield of 2,3-dihydro-2,2-dimethyl-7-benzofuranyl chloroformate and the amount of sodium hydroxide consumed with and without aqueous phase removal. Lower than theoretical chlorofermate/sodium hydroxide ratios evidence excess phosgene hydrolysis.

Preparation of 2,3-Dihydro-2,2-Dimethyl-7-Benzofuranyl Chloroformate Without Aqueous Phase Removal A solution of 83.7 grams (0.51 moles) of 2,3-dihydro-2,2-dimethyl-7-benzofuranol in 328 mL of toluene was placed in a flask fitted with an air-driven stirrer, a pH probe, a thermometer, and two inlets. The flask and its contents were cooled to 0°-5° C. At this temperature 75.0 grams (0.765 mole) of liquid phosgene was introduced into the flask. Stirring was started and maintained at a speed of 550 RPM. The temperature of the reaction mixture was allowed to rise to 18°-22° C. and was maintained within this range for the remainder of the reaction. A 30% aqueous solution of sodium hydroxide was pumped into the flask at an average rate of 0.657 mL/min (0.00492 mole/min), the rate being varied sufficiently to maintain the reaction temperature in the selected range. This addition of aqueous sodium hydroxide required 160 minutes during which a total of 98 mL (0.735 mole) of sodium hydroxide was added to the reaction mixture. During the addition the pH remained below zero, but rose abruptly at the conclusion to a pH of 8.3. Samples were removed from the reaction mixture periodically during the sodium hydroxide addition and at the conclusion of the reaction. These samples were analyzed by gas chromatography. Analysis of the final sample provided the following results excluding the solvent peak as measured by peak area percent: 11.3% 2,3-dihydro-2,2-dimethyl-7-benzofuranol; 86.7% 2,3-dihydro-2,2-dimethyl-7-benzofuranyl chloroformate, 1.6% bis(2,3-dihydro-2,2-dimethyl-7-benzofuranyl) carbonate. Sodium hydroxide consumption vs chloroformate production during the reaction is shown in FIG. 1.

EXAMPLE 2

Preparation of 2,3-Dihydro-2,2-Dimethyl-7-Benzofuranyl Chloroformate with Aqueous Phase Removal The procedure of Example 1 was modified in the following ways. A stream of the reaction mixture was pumped from the flask at 30 mL/min into a Dean Stark trap from which the water that separated was withdrawn. The addition rate of aqueous sodium hydroxide to the flask was varied more than in Example 1 and actually ceased for 4-5 minutes on two occasions to maintain the temperature in the 18°-22°C. range. Also, the pH did not remain below zero for the entire experiment, but rose close to, or slightly above neutral when 88% of the sodium hydroxide had been added. In this experiment 82.13 grams (0,500 mole) of 2,3-dihydro-2,2-dimethyl-7-benzofuranol was dissolved in 326 mL of toluene. To this was added 74 grams (0,748 mole) of liquid phosgene at 0°-5° C. The addition of 30% aqueous sodium hydroxide required a total of 132 minutes during which the temperature was maintained in the 18°-22°C. range. A total of 75.4 mL (0,566 mole) of aqueous sodium hydroxide was added to the reaction. Gas chromatographic analysis of the reaction mixture at the conclusion of the reaction provided the following results excluding the peak for the solvent (peak area percent): 0.8% 2,3-dihydro-2,2-dimethyl-7-benzofuranol; 98.4% 2,3-dihydro-2,2-dimethyl-7-benzofuranyl chloroformate, and 0.3% bis(2,3-dihydro-2,2-dimethyl-7-benzofuranyl) carbonate. Sodium hydroxide consumption vs chloroformate production during the reaction is shown in FIG. 1.

EXAMPLE 3

Large Scale Preparation of
2,3-Dihydro-2,2-Dimethyl-7-Benzofuranyl
Chloroformate Without aqueous Phase Removal Charged to a 114 liter, glass-lined reactor equipped with a retreat-blade agitator and finger baffle was 48.85 Kg of toluene and 12.25 Kg (74.6 moles) of 2,3-dihydro-2,2-dimethyl-7-benzofuranol. This mixture was cooled to 10° C., and 11.11 Kg of liquid phosgene was added to the mixture during a 50 minute period. The agitator was operated at 125 rpm. Addition of a 25% aqueous solution of sodium hydroxide was then started while maintaining the reaction temperature at 18°-22° C. The rate of addition of this sodium hydroxide solution was 0.076 Kg/min. After nearly four hours the addition of sodium hydroxide solution was stopped, and a sample of the reaction mixture was removed and analyzed by gas chromatography. This analysis showed that the phosgene had been consumed and that 9% of the 2,3-dihydro-2,2-dimethyl-7-benzofuranol remained unreacted. Therefore, an additional 0.86 Kg of phosgene was added to the reaction mixture. The addition of aqueous sodium hydroxide solution was resumed for a period of 26 minutes. A second sample of the reaction mixture was removed and analyzed by gas chromatography. This analysis indicated that the amount of unreacted 2,3-dihydro-2,2-dimethyl-7-benzofuranol had been reduced, but 4% remained unreacted. Additional aqueous sodium hydroxide was added during a 25 minute period and a third sample was removed. Gas chromatographic analysis showed that the amount of 2,3-dihydro-2,2-dimethyl-7-benzofuranol had decreased to 2.7% and the phosgene had been depleted. An additional 0.54 Kg of phosgene was added, and addition of sodium hydroxide solution was resumed for 13 minutes. A fourth sample was removed. Analysis by gas chromatography showed that the sample contained 1.9% of 2,3-dihydro-2,2-dimethyl-7-benzofuranol. Two more additions of aqueous sodium hydroxide, 0.68 and 0.45 Kg, respectively, completed the reaction. Water (6.80 Kg) was added to dissolve any salts that had solidified. After removing the aqueous phase, the organic phase was washed twice with 18.14 Kg of water. During the reaction a total of 12.52 Kg (126.6 moles) of phosgene and 21.41 Kg (133.8) moles) of 25% aqueous sodium hydroxide had been added. The organic layer which was removed from the reactor weighed 4.18 Kg. A final wt/wt gas chromatographic analysis showed that 98.7% of the 2,3-dihydro-2,2-dimethyl-7-benzofuranol had been reacted. The yield of 2,3-dihydro-2,2-dimethyl-7-benzofuranyl chloroformate was 4.6% and bis(2,3-dihydro-2,2-dimethyl-7-benzofuranyl) carbonate, 2.6%.

EXAMPLE 4

Large Scale Preparation of
2,3-Dihydro-2,2-Dimethyl-7-Benzofuranyl
Chloroformate with Aqueous Phase Removal The reactor used in Example 3 was modified by the addition of an external loop containing a pump, a glass decanter, and a Teflon ®-lined hose. The decanter was constructed to permit removal of water from it while returning the organic phase to the reaction mixture. A portion of the reaction mixture was pumped through this loop at a rate of 11.4-15.1 L/min. Removal of the water required that some water be added to the decantor to dissolve by-product salts. The same amounts of toluene, 2,3-dihydro-2,2-dimethyl-7-benzofuranol, and liquid phosgene were charged to the reactor which was operated under the same conditions as in Example 3. One gallon of water was placed in the decanter prior to starting the addition of the 25% aqueous sodium hydroxide solution. During a period of slightly more than three hours 16.32 Kg of sodium hydroxide solution was added to the reactor. At this point a sample of the reaction mixture was removed for gas chromatographic analysis which showed there was 1.8% of 2,3-dihydro-2,2-dimethyl-7-benzofuranol present. Addition of 0.50 Kg of sodium hydroxide solution during a five minute period was followed by the removal of a second sample for analysis. This sample contained 1.1% of 2,3-dihydro-2,2-dimethyl-benzofuranol. An additional 0.32 Kg of sodium hydroxide solution was added, and a third sample of the reaction mixture was removed for gas chromatographic analysis. The concentration of 2,3-dihydro-2,2 dimethyl-7-benzofuranol had been reduced to 0.7% Finally, 0.23 Kg of the sodium hydroxide solution was added to complete the reaction. The amount of 2,3-dihydro-2,2-dimethyl-7-benzofuranol remaining unreacted was 0.6%. The total weight of 25% aqueous sodium hydroxide solution added during this run was 17.32 Kg (108.3 moles). The organic phase isolated from this reaction weighed 64.5 Kg. A final wt/wt gas chromatographic analysis of the organic phase showed that 99 5% of the 2,3-dihydro-2,2-dimethyl-7-benzofuranol had been reacted. The yield of 2,3-dihydro-2,2-dimethyl-7-benzofuranyl chloroformate was 97.2% and bis(2,3-dihydro-2,2-dimethyl-7-benzofuranyl) carbonate was only 0.2%.

EXAMPLE 5

Preparation of
2,3-Dihydro-2,2-Dimethyl-7-Benzofuranyl-N-Methylcarbamate from 2,3-Dihydro-2,2-Dimethyl
7-Benzofuranyl Chloroformate In a flask was placed 372.3 grams (0.39 mole) of toluene containing 23.6% of 2,3-dihydro-2,2-dimethyl-7-benzofuranyl chloroformate (prepared according to the method of Example 1). This material was cooled to 15° C. To this flask was then added 34.1 grams (0.44 mole) of a 40% aqueous solution of methylamine during a 37 minute period. Upon completion of this addition, 57.0 grams (0.29 mole) of a 20% aqueous solution of sodium hydroxide was added to the reaction mixture during a 93 minute period while maintaining the temperature at 15° C. Upon completion of addition, sufficient 10% aqueous hydrochloric acid was added to the reaction mixture to reduce the pH to 6.2. The reaction mixture was then heated to 80° C. to dissolve all of the 2,3-dihydro-2,2-dimethyl-7-benzofuranyl N-methylcarbamate, and the aqueous phase was separated from the mixture at this temperature. The toluene solution of 2,3-dihydro-2,2-dimethyl-7-benzofuranyl N-methylcarbamate was then cooled to 5° C. to cause the product to crystallize. The solid 2,3-dihydro-2,2-dimethyl-7-benzofuranyl N-methylcarbamate was filtered from the mixture, and the filter cake was washed with cold toluene, yielding, after being dried, 64.2 grams of this product. An additional 14.8 grams of 2,3-dihydro-2,2-dimethyl-7-benzofuranyl N-methylcarbamate was recovered by washing the flask and the filter with acetone and evaporating the solvent. The combined filtrate and toluene washings weighed 223.5 grams.

I claim:

1. An improved process for the production of 2,3-dihydro-2,2-dimethyl-7-benzofuranyl chloroformate which comprises treating, in a reaction zone, a mixture of 2,3-dihydro-2,2-dimethyl-7-benzofuranol and phosgene in a water immiscible organic medium with aqueous base forming an organic phase and an aqueous phase, and removing aqueous phase from the organic phase during the process.

2. The process of claim 1 in which aqueous phase is removed during the treating with aqueous base.

3. The process of claim 2 in which aqueous phase is continuously removed during the entire treating with aqueous base.

4. The process of claim 1 in which the aqueous phase is removed from the organic phase by circulating organic phase and aqueous phase through a liquid-liquid separator and returning organic phase to the reaction zone.

5. The process of claim 4 in which the separator is a centrifugal liquid-liquid separator or a gravity settler.

6. The process of claim 5 in which the gravity settler is a decanter.

7. The process of claim 4 in which 5% to 40% of the organic phase per minute passes through the separator.

8. The process of claim 7 in which 15% to 30% of the organic phase per minute passes through the separator.

9. The process of claim 6 in which aqueous phase is drawn off from the decanter.

10. The process of claim 1 in which aqueous phase is mixed in the organic phase.

11. The process of claim 1 in which the weight/weight ratio of water to organic medium in the reaction zone is less than 0.1.

12. The process of claim 10 in which the weight/weight ratio of water to organic medium in the reaction zone is less than 0.05.

13. The process of claim 12 in which the weight/weight ratio of water to organic medium in the reaction zone is less than 0.02.

* * * * *